(12) United States Patent
Sullivan et al.

(10) Patent No.: US 9,518,001 B1
(45) Date of Patent: Dec. 13, 2016

(54) HIGH PURITY 1,1-DICARBONYL SUBSTITUTED-1-ALKENES AND METHODS FOR THEIR PREPARATION

(71) Applicant: SIRRUS, INC., Loveland, OH (US)

(72) Inventors: Jeffrey M. Sullivan, Goshen, OH (US); Kevin Powers, Cincinnati, OH (US); William Barrett, Bethel, OH (US)

(73) Assignee: SIRRUS, INC., Loveland, OH (US)

( * ) Notice: Subject to any disclaimer, the term of this patent is extended or adjusted under 35 U.S.C. 154(b) by 0 days.

(21) Appl. No.: 15/159,185

(22) Filed: May 19, 2016

Related U.S. Application Data

(60) Provisional application No. 62/335,839, filed on May 13, 2016.

(51) Int. Cl.
| C07C 67/327 | (2006.01) |
| B01J 29/06 | (2006.01) |
| C07C 67/333 | (2006.01) |
| C07C 57/13 | (2006.01) |
| C08G 63/00 | (2006.01) |

(52) U.S. Cl.
CPC ............. *C07C 67/333* (2013.01); *C07C 57/13* (2013.01); *C08G 63/00* (2013.01)

(58) Field of Classification Search
CPC ........ C07C 67/31; C07C 67/56; C07C 67/327; B01J 29/06
See application file for complete search history.

(56) References Cited

U.S. PATENT DOCUMENTS

| 2,212,506 A | 8/1940 | Bachman |
| 2,245,567 A | 6/1941 | Brant et al. |
| 2,403,791 A | 7/1941 | D'Aiello |
| 2,277,479 A | 3/1942 | D'Aiello |
| 2,313,501 A | 3/1943 | Bachman |
| 2,330,033 A | 9/1943 | D'Aiello |

(Continued)

FOREIGN PATENT DOCUMENTS

| CN | 102901754 A | 1/2013 |
| DE | 19508049 A1 | 9/1996 |

(Continued)

OTHER PUBLICATIONS

Takagi et al.: Kogyo Kagaku Zasshi, Reaction of Active Methylene Radicals with Formaldehyde. L. Synthesis of Diethyl Methylenemalonate, 1953, 56, pp. 901-903, English abstract.

(Continued)

*Primary Examiner* — Vu A Nguyen

(74) *Attorney, Agent, or Firm* — The Dobrusin Law Firm, P.C.; Norman L. Sims

(57) ABSTRACT

A composition comprising about 97 mole percent or greater of one or more 1,1-dicarbonyl substituted-1-ethylenes and about 3 mole percent or less of one or more 1,1-dicarbonyl substituted-methanes. A process comprising: contacting in a fluid state one or more 1,1-dicarbonyl substituted-1,1 hydroxymethyl-methanes and greater than 200 ppm to about 1000 ppm of one or more strong acids based on the weight of the one or more 1,1-dicarbonyl substituted-1,1 hydroxymethyl-methanes with a zeolite catalyst at a temperature of about 180° C. to about 220° C. for a sufficient time to convert about 96 percent or greater of the one or more 1,1-dicarbonyl substituted-1,1 hydroxymethyl-methanes to one or more 1,1-dicarbonyl substituted-1-ethylenes.

14 Claims, 1 Drawing Sheet

(56) References Cited

U.S. PATENT DOCUMENTS

| | | |
|---|---|---|
| 3,042,710 A | 7/1962 | Dickstein et al. |
| 3,197,318 A | 7/1965 | Halpern et al. |
| 3,203,915 A | 8/1965 | D'Aiello |
| 3,221,745 A | 12/1965 | Coover et al. |
| 3,427,250 A | 2/1969 | Haas et al. |
| 3,489,663 A | 1/1970 | Bayer et al. |
| 3,523,097 A | 8/1970 | Coover et al. |
| 3,557,185 A | 1/1971 | Ito et al. |
| 3,591,676 A | 7/1971 | Hawkins |
| 3,595,869 A | 7/1971 | Shuman |
| 3,677,989 A | 7/1972 | Jenkinson |
| 3,758,550 A | 9/1973 | Eck et al. |
| 3,923,836 A | 12/1975 | Bender |
| 3,936,486 A | 2/1976 | Egger et al. |
| 3,940,362 A | 2/1976 | Overhults |
| 3,945,891 A | 3/1976 | Aal et al. |
| 3,966,562 A | 6/1976 | Mukushi et al. |
| 3,975,422 A | 8/1976 | Buck |
| 3,978,422 A | 8/1976 | Rheinfelder |
| 3,995,489 A | 12/1976 | Smith et al. |
| 4,001,345 A | 1/1977 | Gorton et al. |
| 4,004,984 A | 1/1977 | Margen |
| 4,018,656 A | 4/1977 | Rogers et al. |
| 4,035,243 A | 7/1977 | Katz et al. |
| 4,036,985 A | 7/1977 | Amato et al. |
| 4,046,943 A | 9/1977 | Smith et al. |
| 4,049,698 A | 9/1977 | Hawkins et al. |
| 4,056,543 A | 11/1977 | Ponticello |
| 4,079,058 A | 3/1978 | Ackermann et al. |
| 4,080,238 A | 3/1978 | Wolinski et al. |
| 4,083,751 A | 4/1978 | Choi et al. |
| 4,102,809 A | 7/1978 | Smith et al. |
| 4,105,688 A | 8/1978 | Arni et al. |
| 4,140,584 A | 2/1979 | Margen |
| 4,148,693 A | 4/1979 | Williamson |
| 4,154,914 A | 5/1979 | Kuraya |
| 4,160,864 A | 7/1979 | Ponticello et al. |
| 4,176,012 A | 11/1979 | Bryant |
| 4,186,058 A | 1/1980 | Katz et al. |
| 4,186,060 A | 1/1980 | Katz et al. |
| 4,198,334 A | 4/1980 | Rasberger |
| 4,224,112 A | 9/1980 | Childs |
| 4,229,263 A | 10/1980 | Childs |
| 4,236,975 A | 12/1980 | Childs |
| 4,237,297 A | 12/1980 | Rody et al. |
| 4,243,493 A | 1/1981 | Gruber et al. |
| 4,256,908 A | 3/1981 | Nishimura et al. |
| 4,282,067 A | 8/1981 | Katz et al. |
| 4,282,071 A | 8/1981 | Sherrod |
| 4,291,171 A | 9/1981 | Baum et al. |
| 4,313,865 A | 2/1982 | Teramoto et al. |
| 4,319,964 A | 3/1982 | Katz et al. |
| 4,329,479 A | 5/1982 | Yabutani et al. |
| 4,396,039 A | 8/1983 | Klenk et al. |
| 4,399,300 A | 8/1983 | Prange et al. |
| 4,411,740 A | 10/1983 | Flaningam et al. |
| 4,440,601 A | 4/1984 | Katz et al. |
| 4,440,910 A | 4/1984 | O'Connor |
| 4,443,624 A | 4/1984 | Prange et al. |
| 4,444,928 A | 4/1984 | Karrer |
| 4,450,067 A | 5/1984 | Angevine et al. |
| 4,504,658 A | 3/1985 | Narisada et al. |
| 4,510,273 A | 4/1985 | Miura et al. |
| 4,517,105 A | 5/1985 | Laemmle et al. |
| 4,539,423 A | 9/1985 | Itatani et al. |
| 4,556,649 A | 12/1985 | Salzburg et al. |
| 4,560,723 A | 12/1985 | Millet et al. |
| 4,578,503 A | 3/1986 | Ishikawa et al. |
| 4,584,064 A | 4/1986 | Ciais et al. |
| 4,613,658 A | 9/1986 | Mathias et al. |
| 4,698,333 A | 10/1987 | Fauss et al. |
| 4,720,543 A | 1/1988 | McPherson et al. |
| 4,728,701 A | 3/1988 | Jarvis et al. |
| 4,736,056 A | 4/1988 | Smith et al. |
| 4,767,503 A | 8/1988 | Crescentini et al. |
| 4,769,464 A | 9/1988 | Sajtos |
| 4,783,242 A | 11/1988 | Robbins |
| 4,835,153 A | 5/1989 | Kabota et al. |
| 4,897,473 A | 1/1990 | Dombek |
| 4,914,226 A | 4/1990 | Di Trapani et al. |
| 4,931,584 A | 6/1990 | Bru-Magniez et al. |
| 4,932,584 A | 6/1990 | Yamazaki et al. |
| 5,021,486 A | 6/1991 | Galbo |
| 5,039,720 A | 8/1991 | Saatweber et al. |
| 5,064,507 A | 11/1991 | O'Donnell et al. |
| 5,142,098 A | 8/1992 | Bru-Magniez et al. |
| 5,162,545 A | 11/1992 | Etzbach et al. |
| 5,210,222 A | 5/1993 | O'Murchu |
| 5,227,027 A | 7/1993 | Topper |
| 5,259,835 A | 11/1993 | Clark et al. |
| 5,284,987 A | 2/1994 | Sikkenga et al. |
| 5,292,937 A | 3/1994 | Manning et al. |
| 5,312,864 A | 5/1994 | Wenz et al. |
| 5,328,687 A | 7/1994 | Leung et al. |
| 5,334,747 A | 8/1994 | Steffen |
| 5,426,203 A | 6/1995 | Sohn et al. |
| 5,446,195 A | 8/1995 | Pacifici |
| 5,514,371 A | 5/1996 | Leung et al. |
| 5,514,372 A | 5/1996 | Leung et al. |
| 5,550,172 A | 8/1996 | Regula et al. |
| 5,565,525 A | 10/1996 | Morimoto et al. |
| 5,567,761 A | 10/1996 | Song |
| 5,575,997 A | 11/1996 | Leung et al. |
| 5,582,834 A | 12/1996 | Leung et al. |
| 5,624,669 A | 4/1997 | Leung et al. |
| 5,693,621 A | 12/1997 | Toepfer et al. |
| 5,817,742 A | 10/1998 | Toepfer et al. |
| 5,817,870 A | 10/1998 | Haas et al. |
| 5,886,219 A | 3/1999 | Steffen |
| 5,902,896 A | 5/1999 | Bauer |
| 5,952,407 A | 9/1999 | Rasoul et al. |
| 6,069,261 A | 5/2000 | Hoffmann et al. |
| 6,106,807 A | 8/2000 | Albayrak et al. |
| 6,143,352 A | 11/2000 | Clark et al. |
| 6,183,593 B1 | 2/2001 | Narang et al. |
| 6,210,474 B1 | 4/2001 | Romano, Jr. et al. |
| 6,211,273 B1 | 4/2001 | Bru-Magniez et al. |
| 6,225,038 B1 | 5/2001 | Smith et al. |
| 6,238,896 B1 | 5/2001 | Ozaki et al. |
| 6,245,933 B1 | 6/2001 | Malofsky et al. |
| 6,284,915 B2 | 9/2001 | Hirase et al. |
| 6,291,703 B1 | 9/2001 | Schaerfl, Jr. et al. |
| 6,376,019 B1 | 4/2002 | Leung |
| 6,395,737 B1 | 5/2002 | Defossa et al. |
| 6,395,931 B1 | 5/2002 | Carvalho et al. |
| 6,413,415 B1 | 7/2002 | Weiss et al. |
| 6,420,468 B2 | 7/2002 | Bru-Magniez et al. |
| 6,440,461 B1 | 8/2002 | Bru-Magniez et al. |
| 6,512,023 B1 | 1/2003 | Malofsky et al. |
| 6,518,677 B1 | 2/2003 | Capote |
| 6,545,097 B2 | 4/2003 | Pinchuk et al. |
| 6,559,264 B1 | 5/2003 | Konig et al. |
| 6,610,078 B1 | 8/2003 | Bru-Magniez et al. |
| 6,613,934 B1 | 9/2003 | Jegelka et al. |
| 6,673,957 B2 | 1/2004 | Bartek et al. |
| 6,699,928 B2 | 3/2004 | Cobbley et al. |
| 6,716,355 B1 | 4/2004 | Hanemaaijer et al. |
| 6,750,298 B1 | 6/2004 | Bru-Magniez et al. |
| 6,794,365 B2 | 9/2004 | Al-Obeidi et al. |
| 6,841,064 B1 | 1/2005 | Weiss et al. |
| 6,936,140 B2 | 8/2005 | Paxton et al. |
| 7,070,675 B2 | 7/2006 | Schmidt et al. |
| 7,109,369 B2 | 9/2006 | Nose et al. |
| 7,208,621 B2 | 4/2007 | Nose et al. |
| 7,226,957 B1 | 6/2007 | Scranton et al. |
| 7,305,850 B2 | 12/2007 | Tonkovich et al. |
| 7,553,989 B2 | 6/2009 | Sawabe et al. |
| 7,603,889 B2 | 10/2009 | Cypes et al. |
| 7,610,775 B2 | 11/2009 | Tonkovich et al. |
| 7,649,108 B2 | 1/2010 | Schal et al. |
| 7,659,423 B1 | 2/2010 | McArdle |
| 7,663,000 B2 | 2/2010 | Dekkers et al. |
| 7,771,567 B2 | 8/2010 | Rives et al. |
| 7,900,558 B2 | 3/2011 | Yokoi |

(56) References Cited

U.S. PATENT DOCUMENTS

| | | |
|---|---|---|
| 8,609,885 B2 | 12/2013 | Malofsky et al. |
| 8,884,051 B2 | 11/2014 | Malofsky et al. |
| 9,108,914 B1 | 8/2015 | Malofsky et al. |
| 9,181,365 B2 | 11/2015 | Malofsky et al. |
| 9,217,098 B1 | 12/2015 | Stevenson et al. |
| 9,221,739 B2 | 12/2015 | Malofsky et al. |
| 9,234,107 B2 | 1/2016 | Malofsky et al. |
| 9,334,430 B1 | 5/2016 | Stevenson et al. |
| 2001/0005572 A1 | 6/2001 | Lobo et al. |
| 2001/0034300 A1 | 10/2001 | Yurugu et al. |
| 2002/0143128 A1 | 10/2002 | Cabioch et al. |
| 2002/0151629 A1 | 10/2002 | Buffkin et al. |
| 2003/0096069 A1 | 5/2003 | D'Alessio |
| 2003/0199655 A1 | 10/2003 | Yurugi et al. |
| 2004/0076601 A1 | 4/2004 | Bru-Magniez et al. |
| 2004/0082043 A1 | 4/2004 | Yadav |
| 2004/0220060 A1 | 11/2004 | Bartley et al. |
| 2006/0167267 A1 | 7/2006 | Chorghade et al. |
| 2006/0211809 A1 | 9/2006 | Kodemura et al. |
| 2007/0043145 A1 | 2/2007 | Beck et al. |
| 2007/0049655 A1 | 3/2007 | Yoshimune et al. |
| 2007/0092483 A1 | 4/2007 | Pollock |
| 2008/0131618 A1 | 6/2008 | Nakamura et al. |
| 2008/0160305 A1 | 7/2008 | Warren et al. |
| 2008/0187655 A1 | 8/2008 | Markle et al. |
| 2008/0227919 A9 | 9/2008 | Li et al. |
| 2008/0241485 A1 | 10/2008 | Shimohara et al. |
| 2008/0286333 A1 | 11/2008 | Kangas et al. |
| 2009/0203861 A1 | 8/2009 | Lee et al. |
| 2009/0263604 A1 | 10/2009 | Arai et al. |
| 2010/0016508 A1 | 1/2010 | Sasagawa et al. |
| 2010/0256720 A1 | 10/2010 | Overstreet et al. |
| 2010/0286433 A1 | 11/2010 | Malofsky et al. |
| 2010/0286438 A1 | 11/2010 | Malofsky et al. |
| 2011/0015406 A1 | 1/2011 | Umentani et al. |
| 2011/0024392 A1 | 2/2011 | Sato et al. |
| 2011/0164322 A1 | 7/2011 | Morozumi et al. |
| 2012/0083523 A1 | 4/2012 | Richard et al. |
| 2012/0136130 A1 | 5/2012 | Takashima et al. |
| 2013/0281580 A1 | 10/2013 | Malofsky et al. |
| 2013/0303719 A1 | 11/2013 | Malofsky et al. |
| 2014/0058031 A1 | 2/2014 | Overbeek et al. |
| 2014/0248485 A1 | 9/2014 | Malofsky et al. |
| 2014/0275400 A1 | 9/2014 | Chen et al. |
| 2014/0288230 A1 | 9/2014 | Malofsky et al. |
| 2014/0329980 A1 | 11/2014 | Malofsky et al. |
| 2015/0056879 A1 | 2/2015 | Malofsky et al. |
| 2015/0104660 A1 | 4/2015 | Malofsky et al. |
| 2015/0148480 A1 | 5/2015 | Ellison et al. |
| 2015/0210894 A1 | 7/2015 | Malofsky et al. |
| 2015/0303122 A1 | 10/2015 | Malofsky et al. |
| 2015/0361283 A1 | 12/2015 | Malofsky et al. |

FOREIGN PATENT DOCUMENTS

| | | |
|---|---|---|
| FR | 2788516 A1 | 7/2000 |
| GB | 432628 A | 7/1935 |
| GB | 965676 | 8/1964 |
| GB | 965767 | 8/1964 |
| GB | 975733 | 11/1964 |
| JP | H02281013 | 11/1990 |
| JP | H08231564 | 9/1996 |
| JP | 09258448 A | 10/1997 |
| JP | 200019936 | 7/2000 |
| JP | 2008/174494 | 1/2007 |
| WO | 99/46619 | 9/1999 |
| WO | 99/55394 A1 | 11/1999 |
| WO | 2007/120630 A2 | 10/2007 |
| WO | 2010/129068 A1 | 11/2010 |
| WO | 2011/059104 A1 | 5/2011 |
| WO | 2011/161045 A1 | 12/2011 |
| WO | 2012/054616 A2 | 4/2012 |
| WO | 2012/054633 A2 | 4/2012 |
| WO | 2013/059473 | 4/2013 |
| WO | 2013/066629 | 5/2013 |
| WO | 2013/149165 A1 | 10/2013 |
| WO | 2013/149168 A1 | 10/2013 |
| WO | 2013/149173 A1 | 10/2013 |

OTHER PUBLICATIONS

McNab, Kirk-Othmer Encyclopedia of chemical Technology, Pyrolysis, Flash Vacuum, 2009, John Wiley & Sons, Inc., pp. 1-26.

Block, "Diethyl bis (hydroxymethyl) malonate "Organic Syntheses, 1973, Coll. vol. 5, p. 381 [vol. 40, p. 27 (1960); Retrieved on Apr. 4, 2014 from internet: http://www.Orgsyn.org/content/pdfs/procedures/cv5p0381.pdf] p. 381, para 1.

Reddy et al. "An easy-to-use heterogeneous promoted zirconia catalyst for Knoevenagel condensation in liquid phase under solvent-free conditions." Journal of Molecular Catalysts A: Chemical 258 (2006) pp. 302-307.

M. Ware et al.: "DBU: An Efficient Catalyst for Knoeveganel Condensation under Solvent-free Condition," Bulletin of the Catalysis Society of India, (2007), vol. 6, pp. 104-106.

V. G. Nenajdenko et al.: "Reaction of 2-Methylene-1,3-Dicarbonyl Compounds Containing a CF3-Group with 1,3-Dienes," Tetrahedron, (2000), vol. 56, pp. 6549-6556.

J. S. Yadav et al.,: "Phosphane-Catalyzed Knoevenagel Condensation: a Facile Synthesis of a-Cyanoacrylates and a-Cyanoacrylonitriles," Eur, J, Org, Chem. (2004), pp. 546-551.

B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org <http://Euro.J.Org>. Chem., (2006), pp. 3767-3770.

H, A, Oskooie et al.: "On Water: an Efficient Knoevenagel Condensation using 12-Tungstophosphoric Acid as a Reusable Green Catalyst," Synthetic Communications, (2006), vol. 36, pp. 2819-2823.

H. Jiang et al.: "Inorganic Zinc Salts Catalyzed Knoevenagel Condensation at Room Temperature without Solvent," Preparative Biochemistry & Biotechnology, (2009), vol. 39, pp. 194-200.

T. Doi et al.: "Synthesis of Dimethyl gloiosiphne A by Way of Palladium-Catalyzed Domino Cyclization," T. Ora <htto://T.Ora>. Chem., (2007), vol. 72, pp. 3667-3671.

H. Jung et al,: "New and General Methods for the Synthesis of Arylmethylene Bis(3-Hydroxy-2-Cyclohexene-1-Ones) and Xanthenediones by EDDA and In(OTf)3-Catalyzed One-Pot Domino Knoevenagei/Michael or Koevenagei/Michaei/Cyclodehydration Reactions," Bull. Korean Chem. Soc. (2009) vol. 30, No. 9, pp. 1989-1995.

P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.

P. Klemarwczyk: "A General Synthesis of 1,1 Disubstituted Electron Deficient Olefins and their Polymer Properties," Polymer,- (1998), vol. 39, No. I, pp. 173-181.

Gill, Charansingh, et al. "Knoevenagel condensation in neutral media: A simple and efficient protocol for the synthesis of electrophillic alkenes catalyzed by anhydrous ferric sulphate with remarkable reusability." Bulletin of the Catalysis Society of India 7 (2008): 153-157.

P, Ballesteros et al.: "D 1-tert-Butyl Methylenemalonate [Propanedioic Acid, Methylene-, bis( 1,1-dimethylethyl)ester]," Organic Syntheses. Coli. (1990), vol. 7, p. 142; (1986) vol. 64, p. 63.

A. M. Vetrova et al.: "Improvement of the Thermal Stability of Cyanoacrylate Adhesives," Polymer Science, Series D, (2009), vol. 2, No. 1, pp. 27-30.

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.

G. Lai et al.: "Ionic Liquid Functionalized Silica Gel: Novel Catalyst and Fixed Solvent," Tetrahedron Letters (2006), vol. 47, pp. 6951-6953.

(56) References Cited

OTHER PUBLICATIONS

J. R. Harjani et al.: "Lewis Acidic Ionic Liquids for the Synthesis of Electrophilic Alkenes; via the Knoevenagel Condensation," Tetrahedron Letters, (2002), vol. 43, pp. 1127-1130.
P. Ballesteros et al.: "Synthesis of DI-tent-Butyl Methylenemalonate, a Sterically Hindered 1,1-Dicarbonyl Alkene," J. Ora <htto://J.Ora>. Chem, (1983), vol. 48, pp. 3603-3605.
M. Matziari et al. Active Methylene Phosphinic Peptides: A new Diversification Approach Organic Letters 2006 vol. 8, No. 11 pp. 2317-2319 May 5, 2006.
Zaragoza Dorwald, Side Reactions in Organic Synthesis, 2005, Wiley-VCH Verlag GmbH & Co., KgaA, Weinheim, Preface. p. IX.
K. Okamura and T. Date, A Facile Conversion of Ethoxydihydropyrans to 4-Cyanoethylisoxazoles, J. Heterocyclic Chem. 33, 383 (1996).
NPL Yamauchi et al. Tetrahedron Asymetry 12, (2001), 3113-3118.
Cristoph Schotes et al. "Cu(I)- and C(II)-Catalyzed Cyclo- and Michael Addition Reactions of Unsaturated [beta]-Ketoesters" The Journal of Organic Chemistry, vol. 76, No. 14 dated Jul. 15, 2011 p. 5862-5866.
Alejandro Bugarin et al. "Efficient direct [alpha]-methylenation of carbonyls mediated by dissopropylammonium trifluoroacetate", Chemical Communications, vol. 46, No. 10 dated Jan. 25, 2010.
H. Hoffman et al. "Preparation and Selected Reaction of tery-Butyl 2- Methylene-3-oxoalkanoates" Chem. Ber., vol. 124 dated Jan. 1, 1991, pp. 2475-2480.
M. Yamauchi et al. "Reactivity of 2-Methylene-1, 3-dicarbonyl Compounds. 1,3-Dipolar Cycloaddition Reaction with Ethyl Diazoacetate", Chem. Pham. Bull., vol. 49, No. 12, dated Jun. 25, 2001, pp. 1638-1639.
Lawrence N J et al. "Reaction of Baylis-Hillman products with Swern and Dess-Martin oxidants", Tetrahedron Letters, Pergamon, GB, vol. 42 No. 23 dated Jun. 4, 2001, pp. 3939-3941.
Juliana Vale et al. "Efficient [alpha]-Methylenation of Carbonyl Compounds in Ionic Liquids at Room Temperature", Synlett, vol. 2009, No. 1, Jan. 1, 2009 (Jan. 1, 2009), pp. 75-78, XP055170349, ISSN: 0936-5214, DOI: 10.1055/s-0028-1087389 *table 2; compound 3 *.
P. Breton et al., "New Poly(Methylidudene Malonate 2.1.2) Nanoparticles: Recent Developments", Targeting of Drugs 4, Nato ASI Series, vol. 273, pp. 161-172, 1994.
Limouzin et al., "Anionic Polymerization of n-Butyl Cyanoacrylate in Emulsion and Miniemulsion" Macromolecules, vol. 36, 2003, pp. 667-674.
McCoy, M. "A New Way to Stick" Chemical & Engineering News, vol. 92, Issue 26, Jun. 30, 2014, pp. 17-18, paragraph [2].
Bachman et al., "Diethyl Methylenemalonate" Contirbution from the Research Laboratories of the Eastman Kodak Company, May 17, 1939, pp. 493-501.
"Knoevenagel reaction on a molecular sieve", Li Qifang et al., Chinese Science Bulletin, vol. 12, pp. 914-917.
"Knoevenagel Condensation Over Acidic Zeolite", Zuo Bojun et al., Chinese Journal ofCatalysis, vol. 23 (6), pp. 555-558.
"Comparison of the catalytic activity of MOFs and zeolites in Knoevenagel condensation", Maksym Opanasenko, et al., Catalysis Science & Technology, vol. 3 p. 500-507.
Corey et al. "Total Synthesis of Gibberellic Acid. A Simple Synthesiss of a Key Intermediate", J. Am. Chem. Soc. 1982, 104, 6129-6130.
Krishna et al. "Stereodefined Access to 3-Deoxy Sugars Through a Tandem Baylis-Hillman and Lewis Acid Catalyzed Sequence", European Journal of Organic Chemistry, 2010, 813-817.

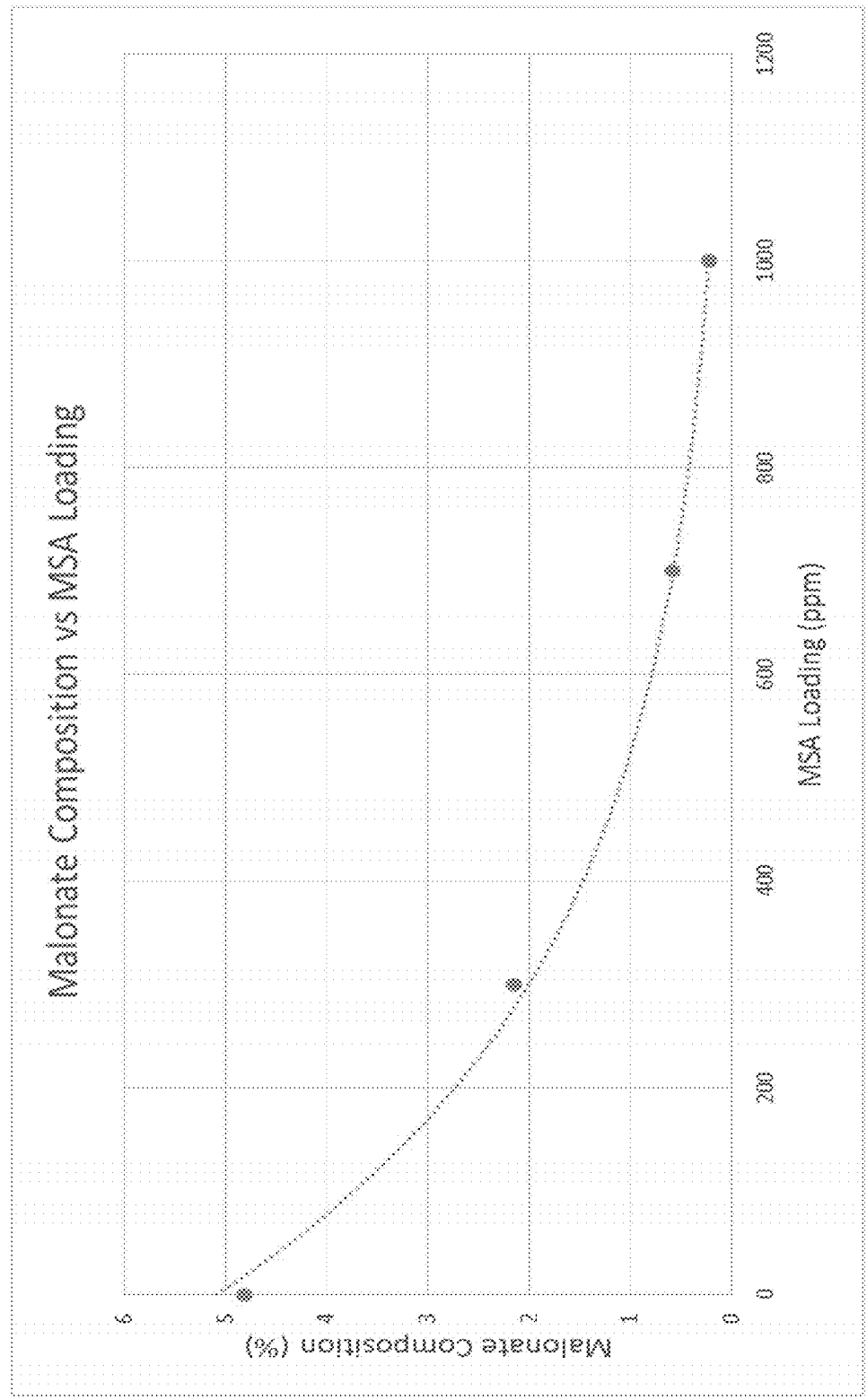

HIGH PURITY 1,1-DICARBONYL SUBSTITUTED-1-ALKENES AND METHODS FOR THEIR PREPARATION

FIELD

Disclosed are compositions containing one or more 1,1-dicarbonyl substituted-1-ethylenes exhibiting high purity and low starting material and by-product content. Further disclosed are processes for the preparation of compositions containing one or more 1,1-dicarbonyl substituted-1-ethylenes exhibiting high purity and low starting material and by-product content.

BACKGROUND 1,1-dicarbonyl substituted-1-ethylenes are of interest because they are capable of polymerizing at ambient temperatures with contact with basic materials. In addition their functional groups provide great flexibility in forming a variety of compounds and polymerizable compositions. 1,1-dicarbonyl substituted-1-ethylenes include methylene malonates. Such compounds have been known since 1886 where the formation of diethyl methylene malonate was first demonstrated by W. H. Perkin, Jr. (Perkin, Ber. 19, 1053 (1886)). The early methods for producing methylene malonates suffer significant deficiencies that preclude their use in obtaining commercially viable monomers, including unwanted polymerization of the monomers during synthesis (e.g., formation of polymers or oligomers or alternative complexes), formation of undesirable side products (e.g., ketals or other latent acid-forming species which impede rapid polymerization), degradation of the product, insufficient and/or low yields, and ineffective and/or poorly functioning monomer product (e.g., poor adhesive characteristics, stability, or other functional characteristics), among other problems. The overall poorer yield, quality, and chemical performance of the monomer products formed by prior methods have impinged on their practical use in the production of the above products. In recent years a number of commonly owned patent applications have been filed which have solved a number of the problems associated with the synthesis of methylene malonates and analogs thereof, for example U.S. Pat. No. 8,609,885 Synthesis of Methylene Malonates Substantially Free of Impurities; U.S. Pat. No. 8,888,051 Synthesis of Methylene Malonates Using Rapid Recovery in the Presence of a Heat Transfer Agent; and U.S. Pat. No. 9,108,914 Method to Obtain Methylene Malonate via Bis(Hydroxymethyl) Malonate Pathway. The synthesis procedures provided therein result in improved yields of heretofore-elusive high quality methylene malonates and other polymerizable compositions.

These applications disclose processes that are capable of producing 1,1-dicarbonyl substituted-1-ethylenes including methylene malonates in high quality which are capable of being used in a variety of high value chemical compositions and formulations. The disclosed processed prepare 1,1-dicarbonyl substituted-1-ethylenes including methylene malonates which contain 6 percent by weight or greater of the starting materials, 1,1-dicarbonyl substituted-methanes including malonates. The starting materials and the desired products have boiling points very close to one another which requires complex and costly processes in terms of capital and operating costs to separate the starting materials from the desired products.

U.S. Pat. No. 9,108,914 discloses preparing methylene malonates in a two-step process wherein the first step comprises reacting a source of formaldehyde with a dialkyl malonate ester in the presence of a reaction catalyst to form a diol reaction product comprising the dialkyl bis(hydroxymethyl) malonate composition; and reacting a dialkyl bis(hydroxyl-methyl) malonate composition in the presence of a suitable catalyst to form a methylene malonate monomer and isolating the methylene malonate monomer. The disclosed catalysts are bases, such as calcium hydroxide exemplified, which need to be removed before the second step to avoid unwanted polymerization of the 1,1-dicarbonyl substituted-1-ethylenes and methylene malonates. Where the catalyst is contains a metal such as, calcium hydroxide, passing the reaction mixture formed through an ion exchange column is used to remove the metals. This step adds both capital costs and increased operating costs due to the need to regenerate the ion exchange resins in the columns.

Thus, what is needed is an improved process that can prepare 1,1-dicarbonyl substituted-1-ethylenes and methylene malonates in higher purity with less starting material in the product produced which allows recovery of high purity material with simpler separation steps to reduce operating and capital costs. What are needed are processes which reduce the operating costs and capital costs of the first step of the process.

SUMMARY

Disclosed are compositions comprising about 97 mole percent or greater of one or more 1,1-dicarbonyl substituted-1-ethylenes and about 3 mole percent or less of one or more 1,1-dicarbonyl substituted-methanes. Disclosed are compositions comprising 98 mole percent or greater of one or more 1,1-dicarbonyl substituted-1-ethylenes and 2 mole percent or less of one or more 1,1-dicarbonyl substituted-methanes. Disclosed are compositions comprising 99 mole percent or greater of one or more 1,1-dicarbonyl substituted-1-ethylenes and 1 mole percent or less of one or more 1,1-dicarbonyl substituted-methanes. The disclosed compositions may contain 1 mole percent or less of an impurity containing a dioxane group, about 1 mole percent or less of any impurity having the alkene group replaced by an analogous hydroxyalkyl group, mole percent is based on the total moles in the 1,1-disubstituted alkene compound.

Disclosed is a process comprising: contacting in a fluid state one or more 1,1-dicarbonyl substituted-1,1-bis (hydroxymethyl)-methanes and greater than 200 ppm to about 1000 ppm of one or more strong acids based on the weight of the one or more 1,1-dicarbonyl substituted-1,1 hydroxymethyl-methanes with a zeolite catalyst at a temperature of about 180° C. to about 220° C. for a sufficient time to convert about 96 percent or greater of the one or more 1,1-dicarbonyl substituted-1,1 hydroxymethyl-methanes to one or more 1,1-dicarbonyl substituted-1-ethylenes. The process may include passing the one or more 1,1-dicarbonyl substituted-1,1 hydroxymethyl-methanes and the one or more strong acids through a fixed bed of zeolite catalyst, a reaction effluent containing one or more 1,1-dicarbonyl substituted-1-ethylenes exits the fixed bed of zeolite catalyst and the one or more 1,1-dicarbonyl substituted-1-ethylenes are isolated from the reaction effluent. The zeolite catalyst may contain acid groups. The strong acid may be present in an amount of about 300 ppm to 900 ppm and about 98 mole percent or greater of the one or more 1,1-dicarbonyl substituted-1,1 hydroxymethyl-methanes are converted to one or more 1,1-dicarbonyl substituted-1-ethylenes. The strong acid may be present in an amount of about 600 ppm to 800 ppm and about 98.5 mole percent or greater of the one or more 1,1-dicarbonyl substituted-1,1 hydroxymethyl-methanes are converted to one or more 1,1-dicarbonyl substituted-1-ethylenes. About 99 mole percent, or about 99.5 mole percent of the one or more 1,1-dicarbonyl substituted-1,1 hydroxymethyl-methanes are converted to one or more 1,1-dicarbonyl substituted-1-ethylenes. The one or more 1,1-dicarbonyl substituted-methanes may be one or more malonates and the one or more 1,1-dicarbonyl substituted-1-ethylenes may be one or more methylene malonates.

The one or more 1,1-dicarbonyl substituted-1-ethylenes may be isolated by separating the reaction effluent into three streams, a light stream comprising water, formaldehyde and one or more 1,1-dicarbonyl substituted-1,1-bis (hydroxymethyl)-methanes; a heavy stream containing oligomers and polymers and an intermediate stream containing one or more 1,1-dicarbonyl substituted-1-ethylenes and one or more 1,1-dicarbonyl substituted-1,1-bis (hydroxymethyl)-methanes; distilling the intermediate stream and isolating a product containing 1,1-dicarbonyl substituted-1-ethylenes. The product isolated may comprise about 97 mole percent by weight or greater of one or more 1,1-dicarbonyl substituted-1-ethylenes and about 3 mole percent by weight or less of one or more 1,1-dicarbonyl substituted-methanes. The product isolated may comprise 98 mole percent by weight or greater of one or more 1,1-dicarbonyl substituted-1-ethylenes and mole 2 percent by weight or less of one or more 1,1-dicarbonyl substituted-methanes. The product isolated may comprise 99 mole percent by weight or greater of one or more 1,1-dicarbonyl substituted-1-ethylenes and 1 mole percent by weight or less of one or more 1,1-dicarbonyl substituted-methanes. The isolated product may contain 1 mole percent or less of an impurity containing a dioxane group, about 1 mole percent of less of any impurity having the alkene group replaced by an analogous hydroxyalkyl group wherein mole percent is based on the total moles in the 1,1-disubstituted alkene compound. The one or more 1,1-dicarbonyl substituted-methanes may be one or more malonates and the one or more 1,1-dicarbonyl substituted-1-ethylenes is one or more methylene malonates.

The one or more 1,1-dicarbonyl substituted-1,1-bis (hydroxymethyl)-methanes may be prepared by contacting one or more 1,1-dicarbonyl substituted-methanes with formaldehyde or a source of formaldehyde in the presence of a catalytic amount of one or more trialkylene amines under conditions to prepare a reaction mixture containing one or more 1,1-dicarbonyl substituted-1,1-bis (hydroxymethyl)-methanes and the trialkylene amines are removed from the reaction mixture by evaporation. The concentration of the trialkylene amine in the one or more 1,1-dicarbonyl substituted-1,1-bis (hydroxymethyl)-methanes is less than 1 ppm based on the weight of the 1,1-dicarbonyl substituted-1,1-bis (hydroxymethyl)-methanes after the trialkylene amines are removed by evaporation.

Disclosed is a composition comprising a polymer of one or more 1,1-dicarbonyl substituted-1-ethylenes containing about 3 mole percent or less of one or more 1,1-dicarbonyl substituted-methanes.

The compositions disclosed exhibit higher purity levels than previously possible. The higher purity levels result in compositions that are capable of preparing polymers having lower polydispersities and higher molecular weights than previously available. The compositions when polymerized prepare polymers having a polydispersity of about 3 or less and a weight average molecular weight of about 10,000 daltons or greater. The higher purity levels allow greater control of polydispersity and molecular weights. The processes disclosed facilitate the preparation of the compositions disclosed having higher purities. The processes also may eliminate unit operations and reduce the complexity of isolation of the desired products and thus reduce the capital costs and operating costs of the process.

DESCRIPTION OF THE DRAWING

FIG. 1 shows a graph of the concentration of malonate in methylene malonate at different concentrations of methane sulfonic acid.

DETAILED DESCRIPTION

The explanations and illustrations presented herein are intended to acquaint others skilled in the art with the invention, its principles, and its practical application. The specific embodiments of the present disclosure as set forth are not intended to be exhaustive or limit the scope of the disclosure. The scope of the disclosure should be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

Disclosed are compositions comprising about 97 percent by weight or greater of one or more 1,1-dicarbonyl substituted-1-ethylenes and about 3 percent by weight or less of one or more 1,1-dicarbonyl substituted-methanes wherein the composition can be prepared with less of the one or more 1,1-dicarbonyl substituted-methanes present in the reaction mixture formed. This reduces the processing costs and capital required to prepare such a composition. The process comprises contacting in a fluid state one or more 1,1-dicarbonyl substituted-1,1-bis (hydroxymethyl)-methanes and greater than 200 ppm to about 1000 ppm of one or more strong acids based on the weight of the one or more 1,1-dicarbonyl substituted-1,1-bis (hydroxymethyl)-methanes with a zeolite catalyst at a temperature of about 180° C. to about 220° C. for a sufficient time to convert about 96 percent or greater of the one or more 1,1-dicarbonyl substituted-1,1-bis (hydroxymethyl)-methanes to one or more 1,1-dicarbonyl substituted-1-ethylenes. Disclosed in a process for preparing the one or more 1,1-dicarbonyl substituted-1,1-bis (hydroxymethyl)-methanes by contacting one or more 1,1-dicarbonyl substituted-methanes with formaldehyde or a source of formaldehyde in the presence of a catalytic amount of one or more trialkylene amines under conditions to prepare a reaction mixture containing one or more 1,1-dicarbonyl substituted-1,1-bis (hydroxymethyl)-methanes and the trialkylene amines are removed from the reaction mixture by evaporation. This process allows the elimination of the need for removal of metal ions by passing the reaction mixture through an ion exchange column.

The compositions disclosed may further comprise any one or more of the features described in this specification in any combination, including the preferences and examples listed in this specification, and includes the following features: a composition comprising 98 mole percent or greater of one or more 1,1-dicarbonyl substituted-1-ethylenes and 2 mole percent or less of one or more 1,1-dicarbonyl substituted-methanes; a composition comprising 99 mole percent or greater of one or more 1,1-dicarbonyl substituted-1-ethylenes and 1 mole percent or less of one or more 1,1-dicarbonyl substituted-methanes; such compositions containing 1 mole percent or less of an impurity containing a dioxane group, about 1 mole percent of less of any impurity having the alkene group replaced by an analogous hydroxyalkyl group wherein mole percent is based on the total moles in the 1,1-disubstituted alkene compound; such compositions that when polymerized prepares a polymer having a polydispersity of about 3 or less and a weight average molecular weight of about 10,000 daltons or greater; the one or more 1,1-dicarbonyl substituted-methanes is one or more malonates and the one or more 1,1-dicarbonyl substituted-1-ethylenes is one or more methylene malonates; A composition comprising a polymer from the abovementioned compositions; composition comprising a polymer of one or more 1,1-dicarbonyl substituted-1-ethylenes containing about 2 mole percent or less of one or more 1,1-dicarbonyl substituted-methanes; and composition comprising a polymer of one or more 1,1-dicarbonyl substituted-1-ethylenes containing about 1 mole percent or less of one or more 1,1-dicarbonyl substituted-methanes.

The methods disclosed may further comprise any one or more of the features described in this specification in any combination, including the preferences and examples listed in this specification, and includes the following features: 1 wherein the one or more 1,1-dicarbonyl substituted-1,1-bis (hydroxymethyl)-methanes and the one or more strong acids are passed through a fixed bed of zeolite catalyst, a reaction effluent containing one or more 1,1-dicarbonyl substituted-1-ethylenes exits the fixed bed of zeolite catalyst and the one or more 1,1-dicarbonyl substituted-1-ethylenes are isolated from the reaction effluent; the zeolite catalyst contains acid groups; the strong acid is present in an amount of about 300 ppm to 900 ppm and about 98 percent or greater of the one or more 1,1-dicarbonyl substituted-1,1-bis (hydroxymethyl)-methanes are converted to one or more 1,1-dicarbonyl substituted-1-ethylenes; the strong acid is present in an amount of about 600 ppm to 800 ppm and about 98.5 percent or greater of the one or more 1,1-dicarbonyl substituted-1, 1-bis (hydroxymethyl)-methanes are converted to one or more 1,1-dicarbonyl substituted-1-ethylenes; the one or more 1,1-dicarbonyl substituted-1,1-bis (hydroxymethyl)-methanes are contacted with the zeolite catalyst in a liquid state or a vapor state; the pKa of the strong acid about 3 to about −12; the strong acid is one or more mineral acids; the one or more 1,1-dicarbonyl substituted-1,1-bis (hydroxymethyl)-methanes and the strong acids are contacted with the bed of the zeolite catalyst at a pressure of about 50 to about 200 mmHg; the one or more 1,1-dicarbonyl substituted-1-ethylenes is isolated by separating the reaction effluent into three streams, a light stream comprising water, formaldehyde and one or more 1,1-dicarbonyl substituted-1,1-bis (hydroxymethyl)-methanes; a heavy stream containing oligomers and polymers and an intermediate stream containing one or more 1,1-dicarbonyl substituted-1-ethylenes and one or more 1,1-dicarbonyl substituted-1,1-bis (hydroxymethyl)-methanes; distilling the intermediate stream and isolating a product containing 1,1-dicarbonyl substituted-1-ethylenes; the residence time of the one or more 1,1-dicarbonyl substituted-1,1-bis (hydroxymethyl)-methanes and the strong acids in the one or more beds of zeolite is about 8 to about 12 minutes; the flow rate of the one or more 1,1-dicarbonyl substituted-1,1-bis (hydroxyl-methyl)-methanes and the strong acids through the beds of zeolite is about 4 to about 7 kg/hour; the one or more 1,1-dicarbonyl substituted-1,1-bis (hydroxymethyl)-methanes are prepared by contacting one or more 1,1-dicarbonyl substituted-methanes with formaldehyde or a source of formaldehyde in the presence of a catalytic amount of one or more trialkylene amines under conditions to prepare a reaction mixture containing one or more 1,1-dicarbonyl substituted-1,1-bis (hydroxymethyl)-methanes and the trialkylene amines are removed from the reaction mixture by evaporation; the concentration of the trialkylene amine in the one or more 1,1-dicarbonyl substituted-1,1-bis (hydroxymethyl)-methanes is less than 1 ppm after the trialkylene amines are removed by evaporation; the trialkylene amine is triethylamine or trimethyl-amine; the one or more 1,1-dicarbonyl substituted-methanes is one or more malonates and the one or more 1,1-dicarbonyl substituted-1-ethylenes is one or more methylene malonates; the product isolated comprises about 97 mole percent or greater of one or more 1,1-dicarbonyl substituted-1-ethylenes and about 3 percent mole percent or less of one or more 1,1-dicarbonyl substituted-methanes; the product isolated comprises 98 mole percent or greater of one or more 1,1-dicarbonyl substituted-1-ethylenes and 2 mole percent or less of one or more 1,1-dicarbonyl substituted-methanes; the product isolated comprises 99 percent by weight or greater of one or more 1,1-dicarbonyl substituted-1-ethylenes and 1 percent by weight or less of one or more 1,1-dicarbonyl substituted-methanes; the product isolated comprises 99.5 percent by weight or greater of one or more 1,1-dicarbonyl substituted-1-ethylenes and 0.5 percent by weight or less of one or more 1,1-dicarbonyl substituted-methanes; the isolated product contains 1 mole percent or less of an impurity containing a dioxane group; and about 1 mole percent of less of any impurity having the alkene group replaced by an analogous hydroxyalkyl group wherein mole percent is based on the total moles in the 1,1-disubstituted alkene compound.

One or more as used herein means that at least one, or more than one, of the recited components may be used as disclosed. Nominal as used with respect to functionality means the theoretical functionality, generally this can be calculated from the stoichiometry of the ingredients used. Generally, the actual functionality is different due to imperfections in raw materials, incomplete conversion of the reactants and formation of by-products. Residual content of a component refers to the amount of the component present in free form or reacted with another material, such as an oligomer or a polymer. Typically, the residual content of a component can be calculated from the ingredients utilized to prepare the component or composition. Alternatively, it can be determined utilizing known analytical techniques. Heteroatom means nitrogen, oxygen, sulfur and phosphorus, more preferred heteroatoms include nitrogen and oxygen. Hydrocarbyl as used herein refers to a group containing one or more carbon atom backbones and hydrogen atoms, which may optionally contain one or more heteroatoms. Where the hydrocarbyl group contains heteroatoms, the heteroatoms may form one or more functional groups well known to one skilled in the art. Hydrocarbyl groups may contain cycloaliphatic, aliphatic, aromatic or any combination of such segments. The aliphatic segments can be straight or branched. The aliphatic and cycloaliphatic segments may include one or more double and/or triple bonds. Included in hydrocarbyl groups are alkyl, alkenyl, alkynyl, aryl, cycloalkyl, cycloalkenyl, alkaryl and aralkyl groups. Cycloaliphatic groups may contain both cyclic portions and noncyclic portions. Hydrocarbylene means a hydrocarbyl group or any of the described subsets having more than one valence, such as alkylene, alkenylene, alkynylene, arylene, cycloalkylene, cycloalkenylene, alkarylene and aralkylene. As used herein percent by weight or parts by weight refer to, or are based on, the weight or the compositions unless otherwise specified.

The term "monofunctional" refers to the first ester compounds (such as 1,1-disubstituted alkene compounds) having only one core unit. The core unit is represented by the combination of the carbonyl groups and the alkylene groups bonded to the 1 carbon atom as shown in Formula 1. The term "difunctional" refers to the first ester compounds or the desired ester product of the reaction, (such as 1,1-disubstituted alkenes compounds) having two core formulas (containing a reactive alkene functionality) bound through a hydrocarbylene linkage between one oxygen atom on each of two core formulas. The term "multifunctional" refers to the first ester compounds or the desired ester product of the reaction (such as 1,1-disubstituted alkene compounds) having more than one core unit (such as reactive alkene functionality) which forms a chain through a hydrocarbylene linkage between one heteroatom, (oxygen atom) or direct bond on each of two adjacent core formulas.

The term "ketal" refers to a molecule having a ketal functionality; i.e., a molecule containing a carbon bonded to two —OR groups, where O is oxygen and R represents any alkyl group or hydrogen. The term "volatile" and "non-volatile" refers to a compound which is capable of evaporating readily at normal temperatures and pressures. The term "non-volatile" refers to a compound which is not capable of evaporating readily at normal temperatures and pressures. The term "stabilized" (e.g., in the context of "stabilized" 1,1-disubstituted alkene compounds or compositions comprising the same) refers to the tendency of the compounds (or their compositions) to substantially not polymerize with time, to substantially not harden, form a gel, thicken, or otherwise increase in viscosity with time, and/or to substantially show minimal loss in cure speed (i.e., cure speed is maintained) with time.

Unless defined otherwise, all technical and scientific terms used herein have the meaning commonly understood by a person skilled in the art to which this disclosure belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991).

The composition disclosed contains any 1,1-dicarbonyl substituted ethylene compounds. 1,1-dicarbonyl substituted ethylene compounds refer to compounds having a carbon with a double bond attached thereto and which is further bonded to two carbonyl carbon atoms. Exemplary compounds are shown in Formula 1:

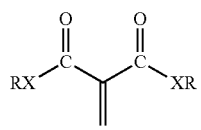

wherein R is a hydrocarbyl group which may contain one or more heteroatoms and X is oxygen or a direct bond (such as a methylene β-ketoester). Exemplary classes of 1,1-dicarbonyl substituted ethylenes are the methylene malonates, methylene beta-keto ester or diketones. Methylene malonates are exemplified by formula 2:

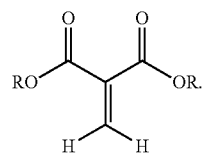

R may be separately in each occurrence alkyl, alkenyl, $C_3$-$C_9$ cycloalkyl, heterocyclyl, alkyl heterocyclyl, aryl, aralkyl, alkaryl, heteroaryl, or alkheteroaryl, or polyoxyalkylene, or both of the Rs form a 5-7 membered cyclic or heterocyclic ring. R may be separately in each occurrence $C_1$-$C_{15}$ alkyl, $C_2$-$C_{15}$ alkenyl, $C_3$-$C_9$ cycloalkyl, $C_{2-20}$ heterocyclyl, $C_{3-20}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene, or both of the R groups form a 5-7 membered cyclic or heterocyclic ring. The recited groups may be substituted with one or more substituents, which do not interfere with the reactions disclosed herein. Preferred substituents include halo alkylthio, alkoxy, hydroxyl, nitro, azido, cyano, acyloxy, carboxy, or ester. R may be separately in each occurrence $C_1$-$C_{15}$ alkyl, $C_3$-$C_6$ cycloalkyl, $C_{4-18}$ heterocyclyl, $C_{4-18}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene. R may be separately in each occurrence a $C_{1-4}$ alkyl. R may be separately in each occurrence methyl or ethyl. R may be the same for each ester group on the 1,1-dicarbonyl substituted ethylenes. Exemplary compounds are dimethyl, diethyl, ethylmethyl, dipropyl, dibutyl, diphenyl, and ethyl-ethylgluconate malonates; or dimethyl and diethyl methylene malonate (R is either methyl or ethyl).

The 1,1-dicarbonyl substituted ethylene compounds disclosed herein exhibit a sufficiently high purity so that it can be polymerized. The purity of the 1,1-dicarbonyl substituted ethylenes may be sufficiently high so that 70 mole percent or more, preferably 80 mole percent or more, more preferably 90 mole percent or more, even more preferably 95 mole percent or more, and most preferably 99 mole percent or more of the 1,1-dicarbonyl substituted ethylenes is converted to polymer during a polymerization process. The purity of the 1,1-dicarbonyl substituted ethylenes is about 96 mole percent or greater, about 97 mole percent or greater, about 98 mole percent or greater, about 99 mole percent or greater, or about 99.5 mole percent or greater, based on the total weight of the 1,1-dicarbonyl substituted ethylenes. The 1,1-dicarbonyl substituted ethylenes contain 4 mole percent or less of 1,1-dicarbonyl substituted-1,1 bis (hydroxymethyl)-methanes, 3 mole percent of less of 1,1-dicarbonyl substituted-1,1 bis (hydroxymethyl)-methanes, 2 mole percent of less of 1,1-dicarbonyl substituted-1,1 bis (hydroxymethyl)-methanes, 1 mole percent of less of 1,1-dicarbonyl substituted-1,1 bis (hydroxymethyl)-methanes, or 0.5 mole percent of less of 1,1-dicarbonyl substituted-1,1 hydroxymethyl-methanes. The concentration of any impurities containing a dioxane group preferably is about 2 mole percent or less, more preferably about 1 mole percent or less, even more preferably about 0.2 mole percent or less, and most preferably about 0.05 mole percent or less, based on the total weight of the 1,1-dicarbonyl substituted ethylenes. The total concentration of any impurity having the alkene group replaced by an analogous hydroxyalkyl group (e.g., by a Michael addition of the alkene with water) preferably is about 3 mole percent or less, more preferably about 1 mole percent or less, even more preferably about 0.1 mole percent or less, and most preferably about 0.01 mole percent or less, based on the total moles in the 1,1-dicarbonyl substituted ethylenes. Preferred 1,1-dicarbonyl substituted ethylenes are prepared by a process including one or more (e.g., two or more) steps of distilling a reaction product or an intermediate reaction product (e.g., a reaction product or intermediate reaction product of a source of formaldehyde and a malonic acid ester).

The compositions disclosed may be prepared by the following process: contacting in a fluid state one or more 1,1-dicarbonyl substituted-1,1 bis (hydroxymethyl)-methanes and greater than 200 ppm to about 1000 ppm of one or more strong acids based on the weight of the one or more 1,1-dicarbonyl substituted-1,1 bis (hydroxymethyl)-methanes with a zeolite catalyst under conditions sufficient to convert about 96 percent or greater of the one or more 1,1-dicarbonyl substituted-1,1 bis (hydroxymethyl)-methanes to one or more 1,1-dicarbonyl substituted-1-ethylenes. The process may be exemplified by equation 1.

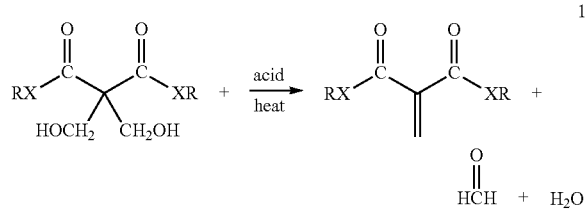

Where the starting material is a bis(hydroxymethyl) malonate and the product is a methylene malonate the process is illustrated by equation 2.

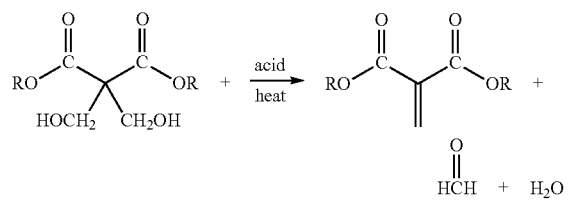

wherein R and X are as described hereinbefore. In the process the hydroxyl methyl groups undergo cracking to form an ethylene group and to generate water and formaldehyde. This reaction is known as a thermolysis reaction. The term "thermolysis" refers to the dissociation of a chemical compound by heat. As used herein, the term "crack," or "cracking" refers to a thermolysis process. The term "cracking reaction" refers to the thermolysis of a 1,1-dicarbonyl substituted-1,1-bis (hydroxymethyl)-methanes to a monomer species with the release of formaldehyde and water. During the process the 1,1-dicarbonyl substituted-1,1-bis (hydroxymethyl)-methanes can also form 1,1-dicarbonyl substituted-methanes thereby reversing the reaction to form the 1,1-dicarbonyl substituted-1,1-bis (hydroxymethyl)-methanes. It is believed that the presence of strong acids in the recited amounts enhance the formation of 1,1-dicarbonyl substituted-1-ethylenes over 1,1-dicarbonyl substituted-methanes.

The acid which may be combined with the 1,1-dicarbonyl substituted-1,1-bis (hydroxymethyl)-methanes can be any acid which reduces the amount of 1,1-dicarbonyl substituted-1,1 bis (hydroxymethyl)-methanes in the reaction product formed in the process and facilitates the formation of the 1,1-dicarbonyl substituted-1-ethylenes. Exemplary acids include mineral acids, such as sulfuric acid and phosphoric acid, such as hydrochloric acid, sulfuric acid, nitric acid, or phosphoric acid, for example, aryl sulfonic acids, including para-toluenesulfonic acid and benzenesulfonic acid, alkyl sulfonic acids, including methanesulfonic acid and trifluoromethanesulfonic acid and the like. Exemplary acids include methyl sulfonic acid, phosphoric acid and sulfuric acid. The acid is present in sufficient amount to facilitate the formation of 1,1-dicarbonyl substituted-1-ethylenes and the reduce the presence of 1,1-dicarbonyl substituted-methanes in the recovered products. The acid is present in an amount of about greater than 200 ppm by weight based on the weight of the 1,1-dicarbonyl substituted-1,1 bis (hydroxymethyl)-methanes, about 300 ppm by weight or greater, about 400 ppm by weight or greater or most preferably about 600 ppm by weight or greater. The acid is present in an amount of about 1000 ppm by weight or less based on the weight of the 1,1-dicarbonyl substituted-1,1 bis (hydroxymethyl)-methanes, about 900 ppm by weight or less or about 800 ppm by weight or less. The acid may be present in an amount of greater than about 1000 ppm but above 1000 ppm does not further improve the selectivity and may result in unnecessarily inhibiting the polymerization of the formed compounds.

The 1,1-dicarbonyl substituted-1,1 bis (hydroxymethyl)-methanes are contacted with the acid in a fluid state, such as liquid or gaseous state or in a liquid state. When contacted in a liquid state the acid and 1,1-dicarbonyl substituted-bis (hydroxymethyl)-methanes are contacted and agitated to form a homogeneous mixture. The 1,1-dicarbonyl substituted-bis (hydroxymethyl)-methanes may be heated to above its melting point to facilitate mixing. The melting point may be above 50° C. The equipment for moving and handling the 1,1-dicarbonyl substituted-1,1 bis (hydroxymethyl)-methanes may be heated to facilitate transport and mixing or the 1,1-dicarbonyl substituted-1,1 bis (hydroxymethyl)-methanes. The 1,1-dicarbonyl substituted-1,1 bis (hydroxymethyl)-methanes and the equipment used to process them may be heated to a temperature of about 50° C. to about 100° C. The resulting mixture may be passed through the bed of zeolite catalyst.

The one or more 1,1-dicarbonyl substituted-1,1 bis (hydroxymethyl)-methanes and one or more strong acids are contacted with zeolite catalyst. The reactants may be contacted with the zeolite catalyst in a bed, the bed may be in a column. The bed may be a fixed bed. The reactants may be flowed through the bed in during the process. The zeolite may be in a particulate form or extruded. The zeolite may have a particle size of about 4 angstroms or greater. The zeolite may be in the acid form having acidic sites in its matrix or pores. The term "zeolite" refers to a molecular sieve containing an alumino silicate lattice, usually in association with some aluminum, boron, gallium, iron, and/or titanium, for example. The ratio of $SiO_2$ to $Al_2O_3$ may be varied in different forms of zeolites. The $SiO_2$ to $Al_2O_3$ ratio in the zeolites used herein may be about 8 or greater. Exemplary zeolites are the ZSM versions and the acid form of such versions are referred to as HZSM's. Exemplary ZSM zeolites include HZSM 5, having a $SiO_2$ to $Al_2O_3$ ratio of about 23 and a pore size of 4 to 6 angstroms; HZSM 22, having a $SiO_2$ to $Al_2O_3$ ratio of about 50 to 100 and a pore diameter of 0.46×0.57 nm; HZSM 12 having a silica to alumina ratio of about 40 and a pore size of 4 to 6 angstroms. The fixed bed is sufficiently long to facilitate conversion of the one or more 1,1-dicarbonyl substituted-1,1-bis (hydroxymethyl)-methanes to one or more 1,1-dicarbonyl substituted-1-ethylenes.

The bed of catalyst is heated to a temperature at which the 1,1-dicarbonyl substituted-1,1-bis (hydroxymethyl)-methanes undergoes cracking to form 1,1-dicarbonyl substituted-1-ethylenes. The bed may be heated by any means that allows the process to proceed, for example by contacting the outside of the fixed bed with a heat transfer fluid. The fixed bed of zeolite may be heated to a temperature of about 180° C. or greater, about 190° C. or greater, about 200° C. or greater, about 210° C. or greater or about 220° C. or greater. The fixed bed of zeolite may be heated to a temperature of about 250° C. or less, about 240° C. or less, or about 230° C. or less. The process is isothermal so it is expected that the bed will exhibit a temperature relatively close to the temperature at which the outside of the catalyst bed is heated. The reactants are flowed through the bed at a flow rate such that the one or more 1,1-dicarbonyl substituted-1,1 bis (hydroxymethyl)-methanes are converted to one or more 1,1-dicarbonyl substituted-1-ethylenes. The flow rate may be about 2 kg/hour or greater, about 3 kg/hour or greater or about 4 kg/hour or greater. The flow rate may be about 10 kg/hour or less, about 8 Kg/hour or less or about 7 kg/hour or less. The reactants may be contacted with the catalyst bed at an internal pressure that facilitates the desired conversion. The pressure in the catalyst bed may be atmospheric or subatmospheric. At subatmospheric pressures a vacuum may be applied to the catalyst bed. The pressure in the bed may be 10 mm/Hg or greater or about 50 mm/Hg or greater. The pressure in the bed may be about 760 mm/Hg or less, about 200 mm/Hg or less or about 150 mm/Hg or less. The one or more 1,1-dicarbonyl substituted-1,1-bis (hydroxymethyl)-methanes and acid mixture has a residence time in the catalyst bed sufficient to convert the one or more 1,1-dicarbonyl substituted-1,1-bis (hydroxyl-methyl)-methanes to one or more 1,1-dicarbonyl substituted-1-ethylenes at the concentrations described herein. The residence time of the one or more 1,1-dicarbonyl substituted-1,1 bis (hydroxymethyl)-methanes and acid mixture in the catalyst bed may be about 5 minutes or greater, about 8 minutes or greater or about 10 minutes or greater. The residence time of the one or more 1,1-dicarbonyl substituted-1,1 hydroxymethyl-methanes and acid mixture in the catalyst bed may be about 20 minutes or less, about 15 minutes or less, or about 12 minutes or less.

The mixture one or more 1,1-dicarbonyl substituted-1,1 bis (hydroxymethyl)-methanes and acid may contain a free radical stabilizer when contacted with catalyst bed to reduce or prevent polymerization during the thermolysis reaction. Any known free radical polymerization stabilizer may be utilized, for instance hydroquinone or the methyl ester of hydroquinone. The free radical stabilizer may be present in a concentration of about 0.1 to 10,000 ppm.

The one or more 1,1-dicarbonyl substituted-1-ethylenes prepared may be isolated using any known processes for recovering such products, see for example Malofsky U.S. Pat. No. 8,609,885; U.S. Pat. No. 8,884,051 and U.S. Pat. No. 9,108,914 all incorporated herein by reference in their entirety or all purposes. The desired products are separated from a variety of by-products, side reaction products and impurities. A variety of separation processes or operations may be utilized. Exemplary separation processes include a series of condensation and distillation steps. Exemplary separation units include, hot condensers, condensers, vacuum distillation apparatuses, simple distillation apparatuses and/or fractional distillation apparatuses. In some exemplary embodiments, the separation techniques may be employed at atmospheric pressure, under vacuum, or under elevated pressure, in accordance with sound engineering principles. The product stream may be separated into a stream of heavy products, comprising oils, oligomers and polymers, a stream of light materials which are volatile, and an intermediate stream containing the desired products and materials that have similar boiling points, such as 1,1-dicarbonyl substituted methanes, e.g. malonates. The cut of heavy materials can be separated as non-volatile reaction bottoms. The light materials may contain water and formaldehyde generated as by-products and are volatile under reaction conditions. The volatile materials can be separated from the product stream and condensed in a condenser. The intermediate stream contains 1,1-dicarbonyl substituted-1-ethylenes and 1,1-dicarbonyl substituted methanes. This cut is subjected to a series of distillations, utilizing fractional distillation columns, and condensations to remove as much of the 1,1-dicarbonyl substituted methanes as economically feasible. With product streams containing more than 4 percent of 1,1-dicarbonyl substituted methanes a number of distillation and condensation steps are required. The product streams of the presently disclosed process exiting the catalyst beds contain less 1,1-dicarbonyl substituted methanes and therefore require less distillations and condensations to remove the 1,1-dicarbonyl substituted methanes. Because there is less 1,1-dicarbonyl substituted methanes the final recovered product contains a higher concentration of the desired products and a lower concentration of the 1,1-dicarbonyl substituted methanes. Also as there are less separation steps required the loss of desired products is lower and the overall yield is higher. State of the art processes cannot prepare product streams with the disclosed purities possible using the process of the instant disclosure as discussed herein.

1,1-dicarbonyl substituted-1,1 bis (hydroxymethyl)-methane (diol) is produced by reacting 1,1-dicarbonyl substituted methanes, malonate ester, and a source of formaldehyde in the presence of a reaction catalyst under suitable reaction conditions. The product, diol, is thereafter collected and treated to prepare for thermolysis for conversion to the desired compounds, 1,1-dicarbonyl substituted-1-ethylene. 1,1-dicarbonyl substituted-1,1 bis (hydroxymethyl)-methane may have hydrocarbyl groups connected to the carbonyl groups by an direct bond or through a heteratom, for example oxygen, the hydrocarbyl groups on each carbonyl group may comprise similar or dissimilar hydrocarbyl groups. The reactants are provided in about a 2:1 molar ratio of formaldehyde to 1,1-dicarbonyl substituted methanes. During the reaction two methylol ($CH_2OH$) groups are added at the active carbon to produce 1,1-dicarbonyl substituted-1,1 bis (hydroxymethyl)-methane (i.e. "diol"). This reaction step may be accomplished in a continuous process. This reaction step may be accomplished without the addition of a solvent. The reaction step may be accomplished at atmospheric pressure. Exemplary sources of formaldehyde include formaldehyde, trioxane, formalin, or paraformaldehyde. The source of formaldehyde may be formalin. The source of formaldehyde may be substantially free of methanol, water, or both. The reaction catalyst may be a basic catalyst. Exemplary reaction catalysts include bases such as calcium hydroxide, calcium carbonate, sodium hydroxide, sodium bicarbonate, amines and polymer supported versions thereof, trialkylamines, trimethyl amine, triethylamine, supported bases such as ion exchange resins. The reaction catalyst may be calcium hydroxide. The diol reaction product may be subjected to a diol purification step prior to contacting the product with the catalyst bed. The diol purification step may comprise cationically exchanging the diol reaction product to produce 1,1-dicarbonyl substituted-1,1 bis (hydroxymethyl)-methane (bis(hydroxymethyl) methylene malonate), subjecting the 1,1-dicarbonyl substituted-1,1 bis (hydroxymethyl)-methane to an evaporation step to remove volatile impurities, or a combination thereof. It may be desirable to cationically exchange the diol reaction product to produce 1,1-dicarbonyl substituted-1,1 bis (hydroxymethyl)-methane, and subjecting the 1,1-dicarbonyl substituted-1,1 bis (hydroxymethyl)-methane to an evaporation step to remove volatile impurities.

Diol may be produced in a continuous flow reactor. A source of formaldehyde/catalyst mixture may be fed into a long static mixer tube. The 1,1-dicarbonyl substituted-methanes may be injected into a plurality of locations in the static mixer tube. It has been discovered that improved conversion to diol is possible through staged addition of the 1,1-dicarbonyl substituted-methanes, in part because the temperature rise due to the exothermic reaction may be more readily controlled. Additionally, the static mixer tube may be maintained in a water bath or other medium to control reaction temperature. The diol production reaction temperature may be maintained at about 30° C. to about 40° C. After sufficient reaction time, the reaction may be quenched to prevent or minimize formation of undesired side products. In an exemplary embodiment, because the diol production reaction is catalyzed by a base, a pH lowering agent may optionally be introduced to quench the reaction. In other exemplary embodiments, the reaction kinetics are such that a quenching agent may not be required. The residence time of the reaction mixture in the reactor is chosen to maximize conversion of the product to 1,1-dicarbonyl substituted-1,1 bis (hydroxymethyl)-methanes. The reaction time may be 5 minutes or greater or 10 or greater. The reaction time may be 30 minutes or less or 20 minutes or less.

Before use in the thermolysis reaction the 1,1-dicarbonyl substituted-1,1-bis (hydroxymethyl)-methanes need to be purified. Where a metal containing catalyst, such as calcium hydroxide, is utilized the 1,1-dicarbonyl substituted-1,1-bis (hydroxymethyl)-methanes may be passed through an ion exchange resin to remove metal ions, cations. The cations are removed to a level wherein the amount of cations present do not interfere in the thermolysis reaction. The level of cations in the 1,1-dicarbonyl substituted-1,1-bis (hydroxymethyl)-methanes may be reduced to about 500 ppm or less, 50 ppm or less or 5 ppm or less. The 1,1-dicarbonyl substituted-1,1-bis (hydroxymethyl)-methanes may further be purified to remove volatile materials such as water or volatile catalysts. The water content may be about 5 percent by weight of the 1,1-dicarbonyl substituted-1,1-bis (hydroxymethyl)-methanes or less, 0.5 percent by weight or less, or about 0.1 percent by weight or less The 1,1-dicarbonyl substituted-1,1 bis (hydroxymethyl)-methanes may be cationically exchanged using an ion-exchange column packed with an ion-exchange resin. The ion exchange column may be a pressurized ion-exchange column. The pressurized ion-exchange column may be pressurized up to 1000 psi. The 1,1-dicarbonyl substituted-1,1-bis (hydroxymethyl)-methanes may be subjected to an evaporation step to remove volatile impurities, such as water. The evaporation step may be performed by a short heat residence time evaporation process, such as wiped-film evaporation, rotary evaporation or horizontal or vertical thin-film evaporation. In particular embodiments, the evaporation step is performed by wiped-film evaporation.

The one or more 1,1-dicarbonyl substituted-1,1 hydroxymethyl-methanes may be prepared by contacting one or more 1,1-dicarbonyl substituted-methanes with formaldehyde or a source of formaldehyde in the presence of a catalytic amount of one or more trialkylene amines under conditions to prepare a reaction mixture containing one or more 1,1-dicarbonyl substituted-1,1 bis (hydroxymethyl)-methanes and the trialkylene amines are removed from the reaction mixture by evaporation. Exemplary trialkylene amines include $C_{1-3}$ trialkyl amines, for example trimethyl amine, triethyl-amine or tripropylene amine. The trialkylene amine may include trimethyl amine or triethyl-amine. After preparation of the one or more 1,1-dicarbonyl substituted-1,1 bis (hydroxymethyl)-methanes the one or more 1,1-dicarbonyl substituted-1,1 hydroxymethyl-methanes are subjected to a process to evaporate away the volatile materials including the trialkyl amine catalyst. After purification the one or more 1,1-dicarbonyl substituted-1,1 bis (hydroxymethyl)-methanes may contain about 5000 ppm or less of trialkyl amine, or about 1 ppm or less of trialkyl amines. The use of trialkyl amines to prepare the one or more 1,1-dicarbonyl substituted-1,1 bis (hydroxymethyl)-methanes may provide an advantage in that the need for purification by ion exchange can be eliminated which reduces capital and operating costs.

The compositions disclosed may be utilized to prepare homo and copolymers. The higher purity of the compositions provide greater control of the homo and copolymers so that desired molecular weights and polydispersities can be prepared. The 1,1-dicarbonyl substituted-methanes in the polymers function to plasticize the polymers, which may be undesirable for many applications. Thus lower amounts of 1,1-dicarbonyl substituted-methanes may result in better control of the properties of the polymers. The polymers contain 3 weight percent or less of 1,1-dicarbonyl substituted-methanes, 2 weight percent or less of 1,1-dicarbonyl substituted-methanes, or 1 weight percent or less of 1,1-dicarbonyl substituted-methanes. The polymers prepared may have molecular weights of about 5,000 daltons or greater, molecular weights of about 10,000 daltons or greater or molecular weights of about 500,000 daltons or greater. The polymers may have molecular weights of about 1,000,000 daltons or less or about 100,000 or less. The polymers prepared may have polydispersities of about 1 or greater. The polymers may have polydispersities of about 3 or less, about 2 or less or about 1.1 or less.

The polymerizable compositions disclosed herein can be polymerized by exposing the composition to free radical polymerization conditions or to anionic polymerization conditions. Free radical polymerization conditions are well known to those skilled in the art such as disclosed in U.S. Pat. No. 6,458,956 incorporated herein by reference. In certain embodiments the polymerizable compositions are exposed to anionic polymerization conditions. The polymerizable compositions are contacted with any anionic polymerization initiator or with any nucleophilic material. As the 1,1-disubstitued substituted-1,1-bis (hydroxymethyl)-methanes are highly electrophilic contact with any nucleophilic material can initiate anionic polymerization. Anionic polymerization is commonly referred to as living polymerization because the terminal portion of the polymeric chains are nucleophilic and will react with any unreacted 1,1-disubstituted substituted-1,1-bis (hydroxymethyl)-methanes they come into contact with. Thus the polymerizable composition will continue until all available unreacted 1,1-disubstitued substituted-1,1-bis (hydroxymethyl)-methanes polymerize or the polymerizing mixture is subjected to a quenching step.

In a quenching step the mixture is contacted with an acid which terminates the polymeric chain ends and stops further polymerization. The polymerization can proceed at any reasonable temperature including at ambient temperatures, from about 20 to 35° C., depending on ambient conditions. The polymerization can be performed in bulk, without a solvent or dispersant, or in a solvent or dispersant.

According to certain embodiments, a suitable polymerization initiator can generally be selected from any agent that can initiate polymerization substantially upon contact with a selected polymerizable composition. In certain embodiments, it can be advantageous to select polymerization initiators that can induce polymerization under ambient conditions and without requiring external energy from heat or radiation. In embodiments wherein the polymerizable composition comprises one or more 1,1-disubstituted alkene compounds, a wide variety of polymerization initiators can be utilized including most nucleophilic initiators capable of initiating anionic polymerization. Exemplary initiators include metal carboxylate salts, alkaline earth carboxylate salts, amines, halides (halogen containing salts), metal oxides, and mixtures containing such salts or oxides. Exemplary anions for such salts include anions based on halogens, acetates, benzoates, sulfur, carbonates, silicates and the like. The mixtures containing such compounds can be naturally occurring or synthetic. Specific examples of exemplary polymerization initiators for 1,1-disubstituted ethylene compounds can include glass beads (being an amalgam of various oxides including silicon dioxide, sodium oxide, and calcium oxide), ceramic beads (comprised of various metals, nonmetals and metalloid materials), clay minerals (including hectorite clay and bentonite clay), and ionic compounds such as sodium silicate, sodium benzoate, and calcium carbonate. Other polymerization initiators can also be suitable including certain plastics (e.g., ABS, acrylic, and polycarbonate plastics) and glass-fiber impregnated plastics. Additional suitable polymerization initiators for such polymerizable compositions are also disclosed in U.S. Patent App. Publication No. 2015/0073110, which is hereby incorporated by reference. In some embodiments the polymerization initiator may be encapsulated using any encapsulation method compatible with the polymerization of the 1,1-disubstituted substituted-1,1-bis (hydroxymethyl)-methanes. In some embodiments the encapsulated initiator (activation agent) may be as disclosed in Stevenson et al. U.S. Pat. No. 9,334,430 incorporated herein by reference in its entirety for all purposes.

Polymerization can be terminated by contacting the polymeric mixture with an anionic polymerization terminator. In some embodiments the anionic polymerization terminator is an acid. In some embodiments it is desirable to utilize a sufficient amount of the acid to render the polymerization mixture slightly acidic, preferably having a pH of less than 7, more preferably less than about 6. Exemplary anionic polymerization terminators include, for example, mineral acids such as methane sulfonic acid, sulfuric acid, and phosphoric acid and carboxylic acids such as acetic acid and trifluoroacetic acid.

The polymerizable compositions may be polymerized in bulk, which is in the absence of a solvent or dispersant, in a solution or in an emulsion. Polymerization in bulk can be performed by contacting the polymerizable composition which may include any of the other ingredients disclosed herein with a suitable substrate and an activator and allowing the composition to polymerize.

The polymerizable compositions may be prepared by emulsion polymerization. For example the polymerizable compositions may be prepared by the process disclosed in Stevenson et al., U.S. Pat. No. 9,249,265 incorporated herein by reference in its entirely for all purposes. Disclosed in Stevenson et al., U.S. Pat. No. 9,249,265 is a process comprising the steps of: agitating a mixture including: about 25 weight percent or more of a carrier liquid, a surfactant (e.g., an emulsifier) and one or more monomers to form micelles of the one or more monomers in the carrier liquid, wherein the one or more monomers includes one or more 1,1-disubstituted alkenes; reacting an activator with at least one of the monomers in the micelle for initiating the anionic polymerization of the one or more monomers; and anionically polymerizing the one or more monomers. The polymerization process preferably includes one or more surfactants for forming an emulsion having micelles or a discrete phase including a monomer (e.g., a 1,1-disubstituted alkene compound) distributed throughout a continuous phase (e.g., a continuous phase including a carrier liquid). The surfactant may be an emulsifier, a defoamer, or a wetting agent. The surfactant preferably is present in a sufficient quantity so that a stable emulsion is formed by mixing or otherwise agitating a system including the monomer and carrier liquid. The surfactants according to the teachings herein include one or more surfactants for improving the stability of emulsion (i.e., for improving the stability of the dispersed phase in the carrier liquid phase). The surfactant and/or the amount of surfactant is preferably selected so that all of the monomer micelles are covered by a layer of the surfactant. The surfactant may include an amphoteric surfactant, a nonionic surfactant, or any combination thereof. The surfactant preferably is free of anionic surfactants during the polymerization process. One example of a preferred surfactant (e.g., an emulsifier) is an ethoxylate, such as an ethoxylated diol. For example, the surfactant may include 2,4,7, 9-tetramethyl-5-decyne-4,7-diol ethoxylate. The surfactant may include a poly(alkene glycol). Another example of a preferred surfactant is a poly(ethylene glycol)-block-poly(propylene glycol)-block-poly(ethylene glycol) copolymer. Another example of a preferred surfactant is a surfactant including an alcohol, an ethoxylated alcohol, or both. For example, the surfactant may include CARBOWET® 138 nonionic surfactant (including alkyl alcohol, polyethylene glycol, ethoxylated $C_9$-$C_{11}$ alcohols). Another example of a preferred surfactant is a surfactant including a sorbitan, a sorbitol, or a polyoxyalkene. For example, the surfactant may include sorbitan monopalmitate (nonionic surfactant). Other examples of preferred surfactants include branched polyoxyethylene (12) nonylphynyl ether (IGEPAL® CO-720) and poly(ethylene glycol) sorbitol hexaoleate (PEGSH). The amount of the surfactant (e.g., the amount of the emulsifier) preferably is sufficient to form a layer that substantially encapsulates the monomer and subsequent polymer particles. The amount of surfactant preferably is sufficient so that the discrete phase has a diameter of about 10 mm or less, about 1 mm or less, about 300 µm or less, or about 100 µm or less. The amount of the surfactant is preferably sufficient so that the discrete phase has a diameter of about 0.01 µm or more, about 0.1 µm or more, about 1 µm or more, about 10 µm or more, or about 50 µm or more. The concentration of the surfactant may be about 0.001 weight percent or more, preferably about 0.01 weight percent or more, more preferably about 0.1 weight percent or more, and most preferably about 0.5 weight percent or more, based on the total weight of the emulsion. The concentration of the surfactant may be about 15 weight percent or less, preferably about 10 weight percent or less, and more preferably about 6 weight percent or less, and most preferably about 3 weight percent or less, based on the total weight of the emulsion. The weight ratio of the surfactant to the total weight of the monomer and polymer in the emulsion (e.g., at the end of the polymerization process) preferably is about 0.0001 or more, more preferably about 0.002 or more, even more preferably about 0.005 or more, and most preferably about 0.01 or more. The weight ratio of the surfactant to the total weight of the monomer and polymer in the emulsion (e.g., at the end of the polymerization process) preferably is about 5 or less (i.e., about 5:1 or less), more preferably about 1 or less, even more preferably about 0.5 or less, and most preferably about 0.1 or less. The carrier liquid is preferably water. The polymerization process may include a step of applying shear forces or sonication to a mixture including at least the surfactant and the carrier fluid for forming an emulsion. For example, the process may include stirring or otherwise agitating the mixture for creating the emulsion.

The polymerizable compositions disclosed herein may be polymerized in solution via anionic polymerization processes. In some embodiments the polymerizable compositions may be polymerized utilizing the method disclosed in Palsule et al. U.S. Pat. No. 9,279,022, incorporated herein in its entirety for all purposes. According to the process disclosed in Palsule et al. U.S. Pat. No. 9,279,022 the process comprises the steps of mixing one or more 1,1-disubstituted alkenes and a solvent; adding an activator; reacting the activator with the one or more 1,1-disubstituted alkenes to initiate the anionic polymerization of the one or more 1,1-disubstituted alkenes; and anionically polymerizing the one or more 1,1-disubstituted alkenes to form a polymer. The concentration of the monomer in the solution polymerization process may be sufficiently low so that after polymerization, the solution can flow. If the concentration of the monomer is too high, the solution becomes too viscous at the end of the polymerization process and the solution may be difficult to handle. The concentration of the monomer in the solution polymerization process may be sufficiently high so that the polymerization process is economical. The one or more monomers is preferably present at a concentration of about 0.5 weight percent or more, more preferably about 2 weight percent or more, even more preferably about 5 weight percent or more, and most preferably about 8 weight percent or more, based on the total weight of the solvent and monomer. The one or more monomers may be present at a concentration of about 90 weight percent or less, preferably about 75 weight percent or less, more preferably about 50 weight percent or less, even more preferably about 30 weight percent or less, and most preferably about 20 weight percent or less. If the monomer is added at multiple times (such as continuous and/or sequential monomer addition), it will be appreciated that the amount of the one or more monomers refers to the total amount of monomer and polymer and by-products of the monomer that are present when the addition of monomer has been completed. The polymerization process includes one or more solvents selected so that the monomer and solvent form a single phase. Preferably the solvent does not chemically react with the other components of the solution polymerization system during the polymerization process. For example, the solvent preferably does not react with the monomer. As another example, the solvent preferably does not react with the activator. Preferred solvents are organic solvents, or mixtures of organic solvents. Such solvents, or solvent mixtures typically are in a liquid state at the reaction temperature(s) (e.g., during activation and/or during polymerization. The pressure of the solvent (e.g., organic solvent) and of the monomer at the polymerization temperature should be sufficiently low so that the risk of the reactor failing from over-pressure is reduced or eliminated. For example the partial pressure of the solvent, of the monomer, or both, at the polymerization temperature may be about 500 Torr or less, about 200 Torr or less, about 50 Torr or less, or about 5 Torr or less. It may be desirable for the solvent to be substantially or entirely free of any solvent that may react with the monomer via Michael addition. However, by selecting reaction conditions so that the polymerization reaction is sufficiently fast, it may be possible to employ such monomers in the solvent polymerization process. For example, by selecting parameters such as monomer feed rates, reaction temperature, monomer type, and pH, it may be possible to employ a solvent including or consisting of a protic solvent, such as an alcohol. The solution polymerization may be initiated using an activator capable of initiating anionic polymerization of the 1,1-disubstituted alkene containing compound. The solvent and/or one or more of the monomers (e.g., the 1,1-disubstituted alkene compounds) may further contain other components to stabilize the monomer prior to exposure to polymerization conditions or to adjust the properties of the final polymer for the desired use. Prior to the polymerization reaction, one or more inhibitors may be added to reduce or prevent reaction of the monomer. Such inhibitors may be effective in preventing anionic polymerization of the monomer, free radical polymerization of the monomer, reaction between the monomer and other molecules (such as water), or any combination thereof.

The polymerization processes disclosed may include a step of applying shear forces to a mixture including at least the monomer and the solvent or carrier. For example, the process may include stirring or otherwise agitating the mixture for creating the solution or emulsion, for dispersing or removing a precipitated polymer, for controlling thermal gradients, or any combination thereof. The polymerization processes preferably include a reaction temperature at which the partial pressure of the solvent is generally low. For example, the partial pressure of the solvent and/or the monomer may be about 400 Torr or less, about 200 Torr or less, about 100 Torr or less, about 55 Torr or less, or about 10 Torr or less. The reaction temperature preferably is about 80° C. or less, more preferably about 70° C. or less, even more preferably about 60° C. or less, even more preferably about 55° C. or less, even more preferably about 45° C. or less, even more preferably about 40° C. or less, and most preferably about 30° C. or less. The reaction temperature typically is sufficiently high that the solvent or carrier liquid and the monomer are in a liquid state. For example, the reaction temperature may be about −100° C. or more, about −80° C. or more, about −30° C. or more, or about 10° C. or more. When polymerizing a 1,1-disubstituted alkene compound, it may be desirable to add one or more acid compounds to the solution, to the monomer, or both, so that the initial pH of the solution is about 7 or less, about 6.8 or less, about 6.6 or less, or about 6.4 or less. The polymerization process may be stopped prior to the completion of the polymerization reaction or may be continued until the completion of the polymerization reaction. Preferably, the reaction rate is sufficiently high and/or the reaction time is sufficiently long so that the polymerization reaction is substantially complete.

The conversion of the monomer to polymer may be about 30 weight percent or more, about 60 weight percent or more, about 90 weight percent or more, about 95 weight percent or more, or about 99 weight percent or more. The conversion of monomer to polymer may be about 100 weight percent or less.

The polymerizable compositions may further contain other components to stabilize the compositions prior to exposure to polymerization conditions or to adjust the properties of the final polymer for the desired use. For example, in certain embodiments, a suitable plasticizer can be included with a reactive composition. Exemplary plasticizers are those used to modify the rheological properties of adhesive systems including, for example, straight and branched chain alkyl-phthalates such as diisononyl phthalate, dioctyl phthalate, and dibutyl phthalate, trioctyl phosphate, epoxy plasticizers, toluene-sulfamide, chloroparaffins, adipic acid esters, sebacates such as dimethyl sebacate, castor oil, xylene, 1-methyl-2-pyrrolidone and toluene. Commercial plasticizers such as HB-40 partially hydrogenated terpene manufactured by Solutia Inc. (St. Louis, Mo.) can also be suitable.

One or more dyes, pigments, toughening agents, impact modifiers, rheology modifiers, natural or synthetic rubbers, filler agents, reinforcing agents, thickening agents, opacifiers, inhibitors, fluorescence markers, thermal degradation reducers, thermal resistance conferring agents, surfactants, wetting agents, or stabilizers can be included in a polymerizable system. For example, thickening agents and plasticizers such as vinyl chloride terpolymer (comprising vinyl chloride, vinyl acetate, and dicarboxylic acid at various weight percentages) and dimethyl sebacate respectively, can be used to modify the viscosity, elasticity, and robustness of a system. In certain embodiments, such thickening agents and other compounds can be used to increase the viscosity of a polymerizable system from about 1 to 3 cPs to about 30,000 cPs, or more.

According to certain embodiments, stabilizers can be included in the polymerizable compositions to increase and improve the shelf life and to prevent spontaneous polymerization. Generally, one or more anionic polymerization stabilizers and or free-radical stabilizers may be added to the compositions. Anionic polymerization stabilizers are generally electrophilic compounds that scavenge bases and nucleophiles from the composition or growing polymer chain. The use of anionic polymerization stabilizers can terminate additional polymer chain propagation. Exemplary anionic polymerization stabilizers are acids, exemplary acids are carboxylic acids, sulfonic acids, phosphoric acids and the like. Exemplary stabilizers include liquid phase stabilizers (e.g., methanesulfonic acid ("MSA")), and vapor phase stabilizers (e.g., trifluoroacetic acid ("TFA")). Free-radical stabilizers preferably include phenolic compounds (e.g., 4-methoxyphenol or mono methyl ether of hydroquinone ("MeHQ") and butylated hydroxy toluene (BHT)). Stabilizer packages for 1,1-disubstituted alkenes are disclosed in U.S. Pat. No. 8,609,885 and U.S. Pat. No. 8,884,051, each incorporated by reference. Additional free radical polymerization inhibitors are disclosed in U.S. Pat. No. 6,458,956 and are hereby incorporated by reference. Generally, only minimal quantities of a stabilizer are needed and, in certain embodiments only about 150 parts-per-million or less can be included. In certain embodiments, a blend of multiple stabilizers can be included such as, for example a blend of anionic stabilizers (MSA) and free radical stabilizers (MeHQ). The one or more anionic polymerization stabilizers are present in sufficient amount to prevent premature polymerization. Preferably, the anionic polymerization stabilizers are present in an amount of about 0.1 part per million or greater based on the weight of the composition, more preferably about 1 part per million by weight or greater and most preferably about 5 parts per million by weight or greater. Preferably, the anionic polymerization stabilizers are present in an amount of about 1000 parts per million by weight or less based on the weight of the composition, more preferably about 500 parts per million by weight or less and most preferably about 100 parts per million by weight or less. The one or more free radical stabilizers are present in sufficient amount to prevent premature polymerization. Preferably, the free radical polymerization stabilizers are present in an amount of about 1 parts per million or greater based on the weight of the composition, more preferably about 5 parts per million by weight or greater and most preferably about 10 parts per million by weight or greater. Preferably, the free radical polymerization stabilizers are present in an amount of about 5000 parts per million by weight or less based on the weight of the composition, more preferably about 1000 parts per million by weight or less and most preferably about 500 parts per million by weight or less.

The polymerizable compositions and polymers disclosed herein may be utilized and a number of applications. Exemplary applications include adhesives, sealants, coatings, components for optical fibers, potting and encapsulating materials for electronics, resins and pre-polymers as raw materials in other systems, and the like.

The polymerizable compositions exhibit a number of advantageous properties including rapid reactivity, room or low temperature reactivity, tailorable rheological characteristics, and the like. Polymers prepared from the polymerizable compositions exhibit a number of advantageous properties including for example, high glass transition temperature, high degradation temperature, high heat resistance, high stiffness and modulus, good rigidity and the like.

Other components commonly used in curable compositions may be used in the compositions of this invention. Such materials are well known to those skilled in the art and may include ultraviolet stabilizers and antioxidants and the like. The compositions of the invention may also contain durability stabilizers known in the art. Among preferred durability stabilizers are alkyl substituted phenols, phosphites, sebacates and cinnamates.

The process disclosed allows the preparation of 1,1-dicarbonyl substituted-1-ethylenes at higher yields than previously possible. The product yield may be 90 percent or greater, 93 percent or greater or 95 percent of greater.

Molecular weights as described herein are number average molecular weights which may be determined by Gel Permeation Chromatography (also referred to as GPC) using a polymethylmethacrylate standard.

ILLUSTRATIVE EMBODIMENTS

The following examples are provided to illustrate the disclosed compositions, but are not intended to limit the scope thereof. All parts and percentages are by weight unless Example Various mixtures of diethyl bis (hydroxymethyl) malonate, heated to above 50° C. so that it is liquid and methylene sulfonic acid are prepared and passed through a bed of HZSM 5 catalyst at a temperature of about 225° C. at a flow rate of 5 Kg/hour. The mixture has a residence time of about 10 minutes. The product streams after exiting the catalyst bed are recovered by distillation. The recovered product streams at each concentration of methane sulfonic acid are collected for a time period of about 1 hour. The recovered streams are analyzed by H-NMR for composition. The following Table shows the concentration of methane sulfonic acid and the concentration of diethyl malonate in the diethyl methylene malonate.

| MSA Loading (ppm) | Malonate in Composition (%) |
|---|---|
| 0 | 4.81 |
| 300 | 2.15 |
| 700 | 0.59 |
| 1000 | 0.22 |

The results are illustrated in FIG. 1. These results illustrate that the addition of a strong acid improves the conversion of diethyl bis (hydroxymethyl) malonate to diethyl methylene malonate and suppresses the conversion of diethyl bis (hydroxymethyl) malonate to diethyl malonate.

Parts by weight as used herein refers to 100 parts by weight of the composition specifically referred to. Any numerical values recited in the above application include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value, and the highest value enumerated are to be considered to be expressly stated in this application in a similar manner. Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

What is claimed is:

1. A process comprising: contacting in a fluid state one or more 1,1-dicarbonyl substituted-1,1-bis (hydroxymethyl)-methanes and greater than 200 ppm to about 1000 ppm of one or more strong acids based on the weight of the one or more 1,1-dicarbonyl substituted-1,1-bis (hydroxymethyl)-methanes with a zeolite catalyst at a temperature of about 180° C. to about 220° C. for a sufficient time to convert about 96 percent or greater of the one or more 1,1-dicarbonyl substituted-1,1-bis (hydroxymethyl)-methanes to one or more 1,1-dicarbonyl substituted-1-ethylenes.

2. A process according to claim 1 wherein the one or more 1,1-dicarbonyl substituted-1,1-bis (hydroxymethyl)-methanes and the one or more strong acids are passed through a fixed bed of zeolite catalyst, a reaction effluent containing one or more 1,1-dicarbonyl substituted-1-ethylenes exits the fixed bed of zeolite catalyst and the one or more 1,1-dicarbonyl substituted-1-ethylenes are isolated from the reaction effluent.

3. A process according to claim 1 wherein the zeolite catalyst contains acid groups.

4. A process according to claim 1 wherein the strong acid is present in an amount of about 300 ppm to 900 ppm and about 98 percent or greater of the one or more 1,1-dicarbonyl substituted-1,1-bis (hydroxymethyl)-methanes are converted to one or more 1,1-dicarbonyl substituted-1-ethylenes.

5. A process according to claim 1 wherein the pKa of the strong acid is about 3 to about −12.

6. A process according to claim 1 wherein the strong acid is one or more mineral acids.

7. A process according to claim 2 wherein the one or more 1,1-dicarbonyl substituted-1,1-bis (hydroxymethyl)-methanes and the strong acids are contacted with the bed of the zeolite catalyst at a pressure of about 50 to about 200 mmHg.

8. A process according to claim 1 wherein the one or more 1,1-dicarbonyl substituted-1-ethylenes is isolated by separating the reaction effluent into three streams, a light stream comprising water, formaldehyde and one or more 1,1-dicarbonyl substituted-1,1-bis (hydroxymethyl)-methanes; a heavy stream containing oligomers and polymers and an intermediate stream containing one or more 1,1-dicarbonyl substituted-1-ethylenes and one or more 1,1-dicarbonyl substituted-1,1-bis (hydroxymethyl)-methanes; distilling the intermediate stream and isolating a product containing 1,1-dicarbonyl substituted-1-ethylenes.

9. A process according to claim 1 wherein the one or more 1,1-dicarbonyl substituted-1,1-bis (hydroxymethyl)-methanes are prepared by contacting one or more 1,1-dicarbonyl substituted-methanes with formaldehyde or a source of formaldehyde in the presence of a catalytic amount of one or more trialkylene amines under conditions to prepare a reaction mixture containing one or more 1,1-dicarbonyl substituted-1,1-bis (hydroxymethyl)-methanes and the trialkylene amines are removed from the reaction mixture by evaporation.

10. A process according to claim 9 wherein the concentration of the trialkylene amine in the one or more 1,1-dicarbonyl substituted-1,1-bis (hydroxymethyl)-methanes is less than 1 ppm after the trialkylene amines are removed by evaporation.

11. A process according to claim 9 wherein the one or more 1,1-dicarbonyl substituted-methanes is one or more malonates and the one or more 1,1-dicarbonyl substituted-1-ethylenes is one or more methylene malonates.

12. A process according to claim 1 wherein the product isolated comprises about 97 mole percent or greater of one or more 1,1-dicarbonyl substituted-1-ethylenes and about 3 percent mole percent or less of one or more 1,1-dicarbonyl substituted-methanes.

13. A process according to claim 12 wherein the product isolated comprises 99 percent by weight or greater of one or more 1,1-dicarbonyl substituted-1-ethylenes and 1 percent by weight or less of one or more 1,1-dicarbonyl substituted-methanes.

14. A process according to claim 12 wherein the isolated product contains 1 mole percent or less of an impurity containing a dioxane group, about 1 mole percent or less of any impurity having the alkene group replaced by an analogous hydroxyalkyl group wherein the mole percent is based on the total moles in the 1,1-disubstituted alkene compound.

* * * * *